US010112012B2

(12) United States Patent
Tu

(10) Patent No.: US 10,112,012 B2
(45) Date of Patent: Oct. 30, 2018

(54) AUTOMATIC REGULATING SYSTEM FOR REGULATION OF LIQUID PRESSURE IN A HUMAN BODY

(71) Applicant: Po-Hsun Tu, New Taipei (TW)

(72) Inventor: Po-Hsun Tu, New Taipei (TW)

( * ) Notice: Subject to any disclaimer, the term of this patent is extended or adjusted under 35 U.S.C. 154(b) by 156 days.

(21) Appl. No.: 15/250,636

(22) Filed: Aug. 29, 2016

(65) Prior Publication Data
US 2018/0055998 A1    Mar. 1, 2018

(51) Int. Cl.
*A61M 31/00* (2006.01)
*A61M 5/172* (2006.01)
*A61M 27/00* (2006.01)

(52) U.S. Cl.
CPC ........ *A61M 5/1723* (2013.01); *A61M 27/006* (2013.01); *A61M 2202/04* (2013.01); *A61M 2202/0464* (2013.01); *A61M 2205/3344* (2013.01); *A61M 2205/3379* (2013.01); *A61M 2210/0693* (2013.01); *A61M 2210/12* (2013.01)

(58) Field of Classification Search
CPC ...... A61M 2205/3379; A61M 5/16831; A61M 5/16854; A61M 5/16886; A61M 5/1723; A61M 27/006; A61M 2202/064; A61M 2205/3344; A61M 2010/0693
See application file for complete search history.

(56) References Cited

U.S. PATENT DOCUMENTS

| 2005/0267413 A1* | 12/2005 | Wang | A61M 5/16831 604/131 |
| 2009/0093774 A1* | 4/2009 | Wang | A61M 5/142 604/247 |
| 2017/0326291 A1* | 11/2017 | Mizutani | A61M 5/142 |

FOREIGN PATENT DOCUMENTS

| CN | 1471413 A | 1/2004 |
| TW | 200538706 A | 12/2005 |

* cited by examiner

*Primary Examiner* — Rebecca E Eisenberg
(74) *Attorney, Agent, or Firm* — DLA Piper LLP (US)

(57) ABSTRACT

An automatic regulating system for regulation of liquid pressure includes a container, a tubing connected between the human tissue and the container, a switch unit controllable to switch between first and second states, a pressure sensor for measuring liquid pressure in the human tissue, a level sensor for detecting a liquid level in the container, and a control module controlling switching of the switch unit according to the liquid pressure and the liquid level detection. Fluid communication between the human tissue and the container is prevented in the first state but is permitted in the second state. Fluid communication between the human tissue and the pressure sensor is permitted in the first state but is prevented in the second state.

20 Claims, 6 Drawing Sheets

AUTOMATIC REGULATING SYSTEM FOR REGULATION OF LIQUID PRESSURE IN A HUMAN BODY

FIELD

The disclosure relates to an automatic regulating system, and more particularly to an automatic regulating system for regulation of liquid pressure in a human body.

BACKGROUND

A conventional regulation approach to maintain constant liquid pressure in a human body is manually operated. For example, when a patient is in circulatory shock, a healthcare provider would measure central venous pressure (CVP) of the patient by connecting a central venous catheter to the inferior vena cava of the patient to obtain a measured pressure value, and supply normal saline into the inferior vena cava via the central venous catheter if the measured pressure value is smaller than a target pressure value. The process of measuring the CVP and the process of supplying normal saline are performed alternately until the measured pressure value increases to the target pressure value or until the normal saline supplied thus far reaches a predetermined amount. The conventional regulation approach generally takes more than an hour, and a dedicated healthcare provider is ideally required. However, due to shortage of manpower in hospitals, the healthcare provider is often busy and multi-tasking, leaving the patient at risk of being oversupplied with normal saline.

Similarly, for a patient who suffers from increased intracranial pressure (ICP) due to traumatic brain injury, stroke or brain tumor, conventional treatment is to connect a catheter to a ventricle of the patient's brain so as to drain cerebrospinal fluid (CSF) from the ventricle for lowering the ICP. The ICP is measured once an hour via the catheter connected to the ventricle, and three to five milliliters of the CSF is drained from the ventricle when a value of the ICP thus measured is greater than a target value. The process of measuring the ICP and the process of draining the CSF are performed alternately until the value of the ICP decreases to the target value or until the drainage accumulated over time reaches a predetermined amount ranging from ten to fifteen milliliters. The conventional treatment takes roughly ten minutes every hour and lasts for several days. Therefore, not only is the conventional treatment time-consuming, but risk of overdrainage is also likely unavoidable under a condition of manpower shortage.

SUMMARY

Therefore, an object of the disclosure is to provide an automatic regulating system for regulation of liquid pressure in a human body that can alleviate at least one of the drawbacks of the prior art.

The automatic regulating system according to the disclosure is configured to be connected to human tissue and includes a container configured to contain liquid, a tubing to be connected between the human tissue and the container, a switch unit, a liquid pressure sensor connected to the switch unit and configured to measure liquid pressure in the human tissue to obtain a liquid pressure value, a level sensor connected to the container and configured to detect a liquid level of the liquid contained in the container, and a control module electrically connected to the switch unit, the liquid pressure sensor and the level sensor.

The tubing includes a first tube which is to be in fluid communication with the human tissue and a second tube which is in fluid communication with the container.

The switch unit is connected between the first tube and the second tube of the tubing, and is controllable to switch between a first conduction state, where fluid communication between the first tube and the second tube of the tubing is prevented while fluid communication between the first tube and the liquid pressure sensor is permitted for allowing the liquid pressure sensor to measure the liquid pressure in the human tissue, and a second conduction state, where the fluid communication between the first tube and the liquid pressure sensor is prevented while the fluid communication between the first tube and the second tube is permitted so that the human tissue is in fluid communication with the container.

The control module is programmed to control switching of the switch unit according to the liquid pressure value obtained by the liquid pressure sensor, and a variation in the liquid level detected by the level sensor.

BRIEF DESCRIPTION OF THE DRAWINGS

Other features and advantages of the disclosure will become apparent in the following detailed description of the embodiments with reference to the accompanying drawings, of which.

DETAILED DESCRIPTION

Figure 1:
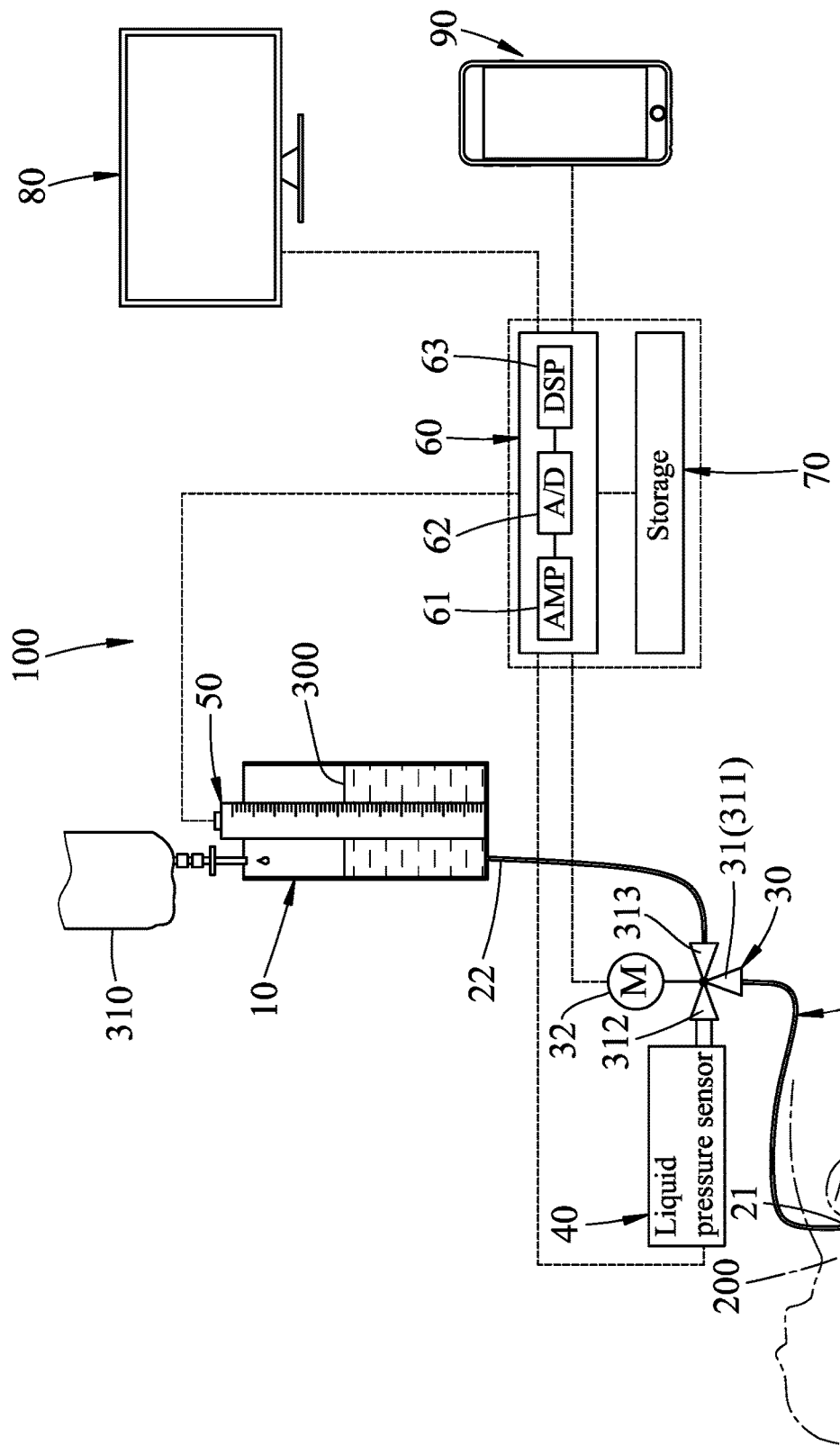
FIG. 1 is a schematic diagram illustrating a first embodiment of an automatic regulating system for regulation of liquid pressure in a human body according to the disclosure.

Before the disclosure is described in greater detail, it should be noted that where considered appropriate, reference numerals or terminal portions of reference numerals have been repeated among the figures to indicate corresponding or analogous elements, which may optionally have similar characteristics.

Figure 2:
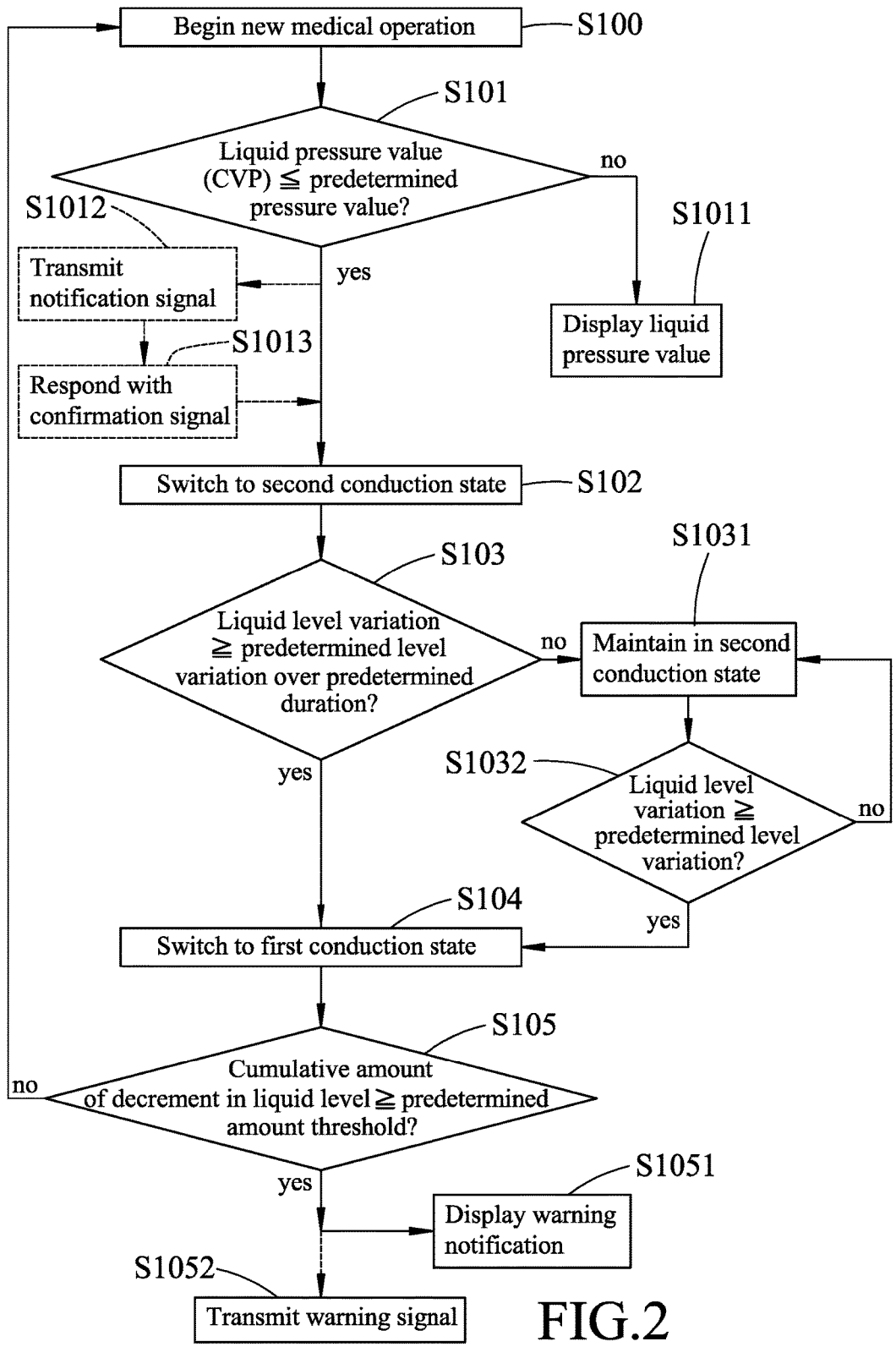
FIG. 2 is a flow chart illustrating a control flow of the first embodiment of the automatic regulating system.

Referring to FIGS. 1 and 2, a first embodiment of an automatic regulating system 100 for regulation of liquid pressure in a human body is illustrated. The automatic regulating system 100 is configured to be connected to human tissue 200, and includes a container 10 configured to contain liquid 300, a tubing 20 to be connected between the human tissue 200 and the container 10, a switch unit 30, a liquid pressure sensor 40 connected to the switch unit 30 and configured to measure liquid pressure in the human tissue 200 to obtain a liquid pressure value, a level sensor 50 connected to the container 10 and configured to detect a liquid level of the liquid 300 contained in the container 10, a control module 60, a storage 70, a display 80, and an electronic device 90 which is configured to communicate with the control module 60. The control module 60 is electrically connected to the switch unit 30, the liquid pressure sensor 40, the level sensor 50, the storage 70, and the display 80.

In this embodiment, the human tissue 200 is exemplified as inferior vena cava in a patient's chest as shown in FIG. 1, and the liquid pressure measured by the liquid pressure sensor 40 is central venous pressure (CVP) in the inferior vena cava. The liquid 300 is saline and is provided by a saline bag 310 which is in fluid communication with the container 10. However, implementation of provision of the liquid 300 is not limited to the disclosure herein.

The tubing 20 includes a first tube 21 which is to be in fluid communication with the human tissue 200 and a second tube 22 which is in fluid communication with the container 10.

The switch unit 30 is connected between the first tube 21 and the second tube 22 of the tubing 20. The switch unit 30 is controllable to switch between a first conduction state, where fluid communication between the first tube 21 and the second tube 22 of the tubing 20 is prevented while fluid communication between the first tube 21 and the liquid pressure sensor 40 is permitted such that a closed communication tube is formed between the human tissue 200 and the liquid pressure sensor 40 for allowing the liquid pressure sensor 40 to measure the liquid pressure in the human tissue 200, and a second conduction state, where the fluid communication between the first tube 21 and the liquid pressure sensor 40 is prevented while the fluid communication between the first tube 21 and the second tube 22 is permitted so that the human tissue 200 is in fluid communication with the container 10. When the switch unit 30 switches to the second conduction state, the liquid pressure sensor 40 is unable to measure the liquid pressure in the human tissue 200.

In this embodiment, the switch unit 30 includes a three-way valve 31 and a step motor 32. The three-way valve 31 has a first terminal 311, a second terminal 312, and a third terminal 313 respectively connected to the first tube 21 of the tubing 20, the liquid pressure sensor 40, and the second tube 22 of the tubing 20. The step motor 32 is electrically connected to the control module 60, and is configured to be controlled by the control module 60 to drive the three-way valve 31 to switch between the first conduction state, where fluid communication between the first terminal 311 and the third terminal 313 is prevented while fluid communication between the first terminal 311 and the second terminal 312 is permitted, and the second conduction state, where fluid communication between the first terminal 311 and the second terminal 312 is prevented while fluid communication between the first terminal 311 and the third terminal 313 is permitted. However, implementation of the switch unit 30 is not limited to this disclosure.

Additionally, in this embodiment, the liquid pressure sensor 40 may be implemented by Transpac® IV Disposable Pressure Transducer manufactured by ICU Medical Incorporation. Therefore, the liquid pressure in the human tissue 200 measured by the liquid pressure sensor 40 is converted thereby to a voltage signal that can be read by the control module 60. However, implementation of the liquid pressure sensor 40 is not limited to the disclosure herein.

Besides, in this embodiment, the level sensor 50 is a resistive liquid level sensor disposed in the container 10, and may be implemented by the liquid level sensor (JLS series) manufactured by Jetec Electronics Co., Ltd. Since resistance of the liquid 300 is inversely proportional to the liquid level thereof, variation in the liquid level of the liquid 300, and variation of volume of the liquid 300 as well, can be determined by the control module 60 according to an increment or decrement in the resistance measured by the level sensor 50. However, implementation of the level sensor 50 is not limited to the disclosure herein.

The control module 60 is programmed to control switching of the three-way valve 31 of the switch unit 30 according to the liquid pressure value obtained by the liquid pressure sensor 40, and according to the variation in the liquid level detected by the level sensor 50.

In this embodiment, the control module 60 is configured to determine whether the liquid pressure value of the liquid pressure (i.e., the CVP) obtained by the liquid pressure sensor 40 is not greater than a predetermined pressure value, e.g., 8-12 cm $H_2O$, and to control the switch unit 30 to switch to the second conduction state for allowing the liquid 300 contained in the container 10 to flow into the human tissue 200 when it is determined by the control module 60 that the liquid pressure value obtained by the liquid pressure sensor 40 is not greater than the predetermined pressure value.

The control module 60 is further configured to determine whether a decrement in the liquid level detected by the level sensor 50 is less than a predetermined level variation, e.g., a level variation corresponding to 250 mL, and to control the switch unit 30 to remain in the second conduction state when it is determined by the control module 60 that the decrement in the liquid level thus detected is less than the predetermined level variation. Conversely, when it is determined by the control module 60 that the decrement in the liquid level thus detected is not less than the predetermined level variation, the control module controls the switch unit 30 to switch to the first conduction state, and determines whether the liquid pressure value is not greater than the predetermined pressure value. It is noted that the decrement in the liquid level detected by the level sensor 50 is defined as the decrement in the liquid level over a predetermined duration, e.g., 20 minutes, of administration of the liquid 300 to the human tissue 200.

Furthermore, the control module 60 is further configured to determine whether a cumulative amount of the decrement in the liquid level, caused by administration of the liquid 300 from the container 10 to the human tissue 200, is smaller than a predetermined amount threshold, e.g., 500 mL.

After determining that the decrement in the liquid level thus detected is not less than the predetermined level variation and after controlling the switch unit 30 to switch to the first conduction state, the control module 60 proceeds to determine whether the liquid pressure value obtained by the liquid pressure sensor 40 is not greater than the predetermined pressure value when determining that the cumulative amount of the decrement in the liquid level is smaller than the predetermined amount threshold.

Moreover, the control module 60 may include, but is not limited to, an amplifier (AMP) 61, an analog-to-digital converter (A/D) 62 electrically connected to the AMP 61, and a digital signal processor (DSP) 63 electrically connected to the A/D 62, so as to process received signals.

In this embodiment, the storage 70 is configured to store settings for system operation, such as the predetermined pressure value, the predetermined level variation, the predetermined amount threshold, the predetermined duration, the liquid pressure value obtained by the liquid pressure sensor 40, and the liquid level detected by the level sensor 50.

In this embodiment, the display 80 is configured to display information corresponding to signals transmitted by the control module 60 for view by a healthcare provider.

In this embodiment, the electronic device 90 is configured to be operated by the healthcare provider and to communicate with the control module 60 by wireless communication, such as Bluetooth. Alternatively, the electronic device 90 may be configured to communicate with the control module 60 in a wired manner. The electronic device 90 may be a smart phone or a tablet, for example.

Figure 3:
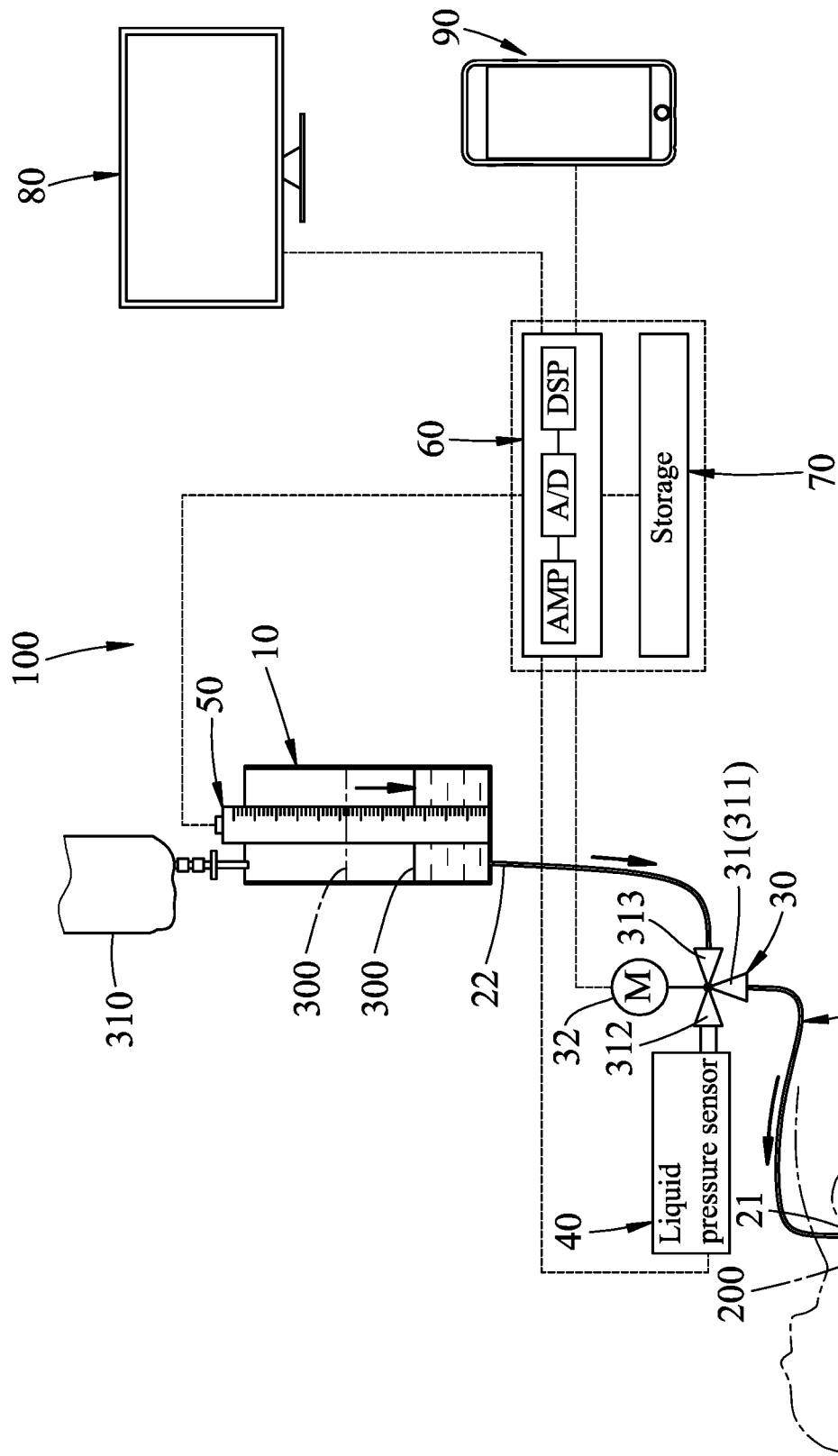
FIG. 3 is a schematic diagram illustrating administration of liquid contained in a container to human tissue in the first embodiment.

Referring to FIGS. 2 and 3, the automatic regulating system 100 is applied to maintain constant CVP of a patient, and a control flow including steps to be performed by the automatic regulating system 100 is illustrated. A predetermined amount, e.g., 500 mL, of the liquid 300 is contained in the container 10 in advance. The first tube 21 is connected to the human tissue 200, and the three-way valve 31 is initially in the first conduction state for allowing the liquid-pressure sensor 40 to measure the liquid pressure in the human tissue 200. The control flow starts from step S100, where a new medical operation begins. In step S101, the control module 60 determines whether the liquid pressure value of the liquid pressure (i.e., the CVP) in the human tissue 200 obtained by the liquid pressure sensor 40 is not greater than the predetermined pressure value.

When it is determined by the control module 60 in step S101 that the liquid pressure value is not greater than the predetermined pressure value, that is, the liquidpressure value of the CVP is too low and the patient is in circulatory shock, the control flow proceeds to step S102. Otherwise, when it is determined by the control module 60 in step S101 that the liquid pressure value is greater than the predetermined pressure value, which means that the liquid pressure value of the CVP of the patient is normal, the control flow proceeds to step S1011.

In step S102, the control module 60 controls the three-way valve 31 to switch from the first conduction state to the second conduction state for allowing the liquid 300 contained in the container 10 to flow into the human tissue 200 by gravity.

In a variation of this embodiment, a double-checking mechanism by the healthcare provider which is exemplified as steps S1012 and S1013 may be adopted for safety concerns. Prior to controlling the switch unit 30 to switch to the second conduction state, in step S1012, the control module 60 transmits a notification signal to the electronic device 90 for output of a notification by the electronic device 90 when it is determined in step S101 that the liquid pressure value obtained by the liquid pressure sensor 40 is not greater than the predetermined pressure value. In step S1013, the healthcare provider who is notified by the notification may, depending on a condition of the patient, respond by operating the electronic device 90 to generate a confirmation signal that is to be transmitted to the control module 60. In other words, the confirmation signal is generated in response to user confirmation of the notification and of the patient's condition. Upon receiving the confirmation signal, step S102 is performed by the control module 60.

In step S103, the control module 60 determines whether the decrement in the liquid level detected by the level sensor 50 over a predetermined duration of administration of the liquid 300 is not less than the predetermined level variation. When it is determined by the control module 60 that the decrement in the liquid level over the predetermined duration is less than the predetermined level variation, which means that a preset amount of the liquid 300 corresponding to the predetermined level variation has not been completely provided to the human tissue 200 from the container 10 within the predetermined duration, the control flow goes to step S1031, where the control module 60 maintains the three-way valve 31 of the switch unit 30 in the second conduction state until it is determined by the control module 60 in step S1032 that the decrement in the liquid level thus detected for the current medical operation is not less than the predetermined level variation. In this way, the preset amount of the liquid 300 contained in the container 10 is ensured to be provided to the human tissue 200.

When it is determined by the control module 60 in step S103 that the decrement in the liquid level over the predetermined duration detected by the level sensor 50 is not less than the predetermined level variation or in step S1032 that the decrement in the liquid level for the current medical operation is not less than the predetermined level variation, which means that the preset amount of the liquid 300 corresponding to the predetermined level variation has been completely provided to the human tissue 200 from the container 10, the control flow goes to step S104, where the control module 60 controls the three-way valve 31 of the switch unit 30 to switch to the first conduction state.

In step S105, after controlling the switch unit 30 to switch to the first conduction state, the control module 60 determines whether the cumulative amount of the decrement in the liquid level is not smaller than the predetermined amount threshold. Herein, the cumulative amount of the decrement is defined as the total decrement amount accumulated in all medical operation (s) performed thus far on this particular patient for bringing his/her CVP back to normal.

When it is determined in step S105 that the cumulative amount of the decrement in the liquid level is smaller than the predetermined amount threshold, which means that the total amount of the liquid 300 provided to the human tissue 200 from the container 10 has not exceeded a safety threshold for treatment, the control flow goes back to step S100 to begin a new medical operation.

In steps S1051 and S1052, the control module 60 controls the display 80 to display a warning notification and transmits a warning signal to the electronic device 90 for output of a warning notification by the electronic device 90 accordingly when it is determined by the control module 60 in step S105 that the cumulative amount of the decrement in the liquid level is not less than the predetermined amount threshold, which means that the total amount of the liquid 300 provided to the human tissue 200 from the container 10 has reached or exceeded the safety threshold for treatment. As a result, the healthcare provider notified by the warning notification may take care of the patient in time and appropriately handle the situation.

In Step S1011, the control module 60 controls the display 80 to display the liquid pressure value, so that the healthcare provider may be informed of the condition of the patient.

Briefly speaking, the control module 60 automatically controls the switching of the three-way valve 31 of the switch unit 30 between the first and second conduction states according to the liquid pressure value obtained by the liquid pressure sensor 40 and the variation in the liquid level detected by the level sensor 50, so that the preset amount of the liquid 300, e.g., the saline, can be provided to the human tissue 200 of the patient in each medical operation. As a result, the liquid pressure value of the CVP of the patient can be brought into a normal range and maintain in the normal range. Therefore, the automatic regulating system 100 of this embodiment is capable of maintaining automatically and precisely constant liquid pressure in the human body and timely informing conditions of the patient. In other words, by means of the automatic regulating system 100 according to the disclosure, workload of the healthcare provider may be alleviated and risk of oversupplying saline in medical treatment may be mitigated.

It is worth noting that the double-checking mechanism by the healthcare provider may be omitted in other embodiments. The electronic device 90 may be omitted in other embodiments as well.

Figure 4:
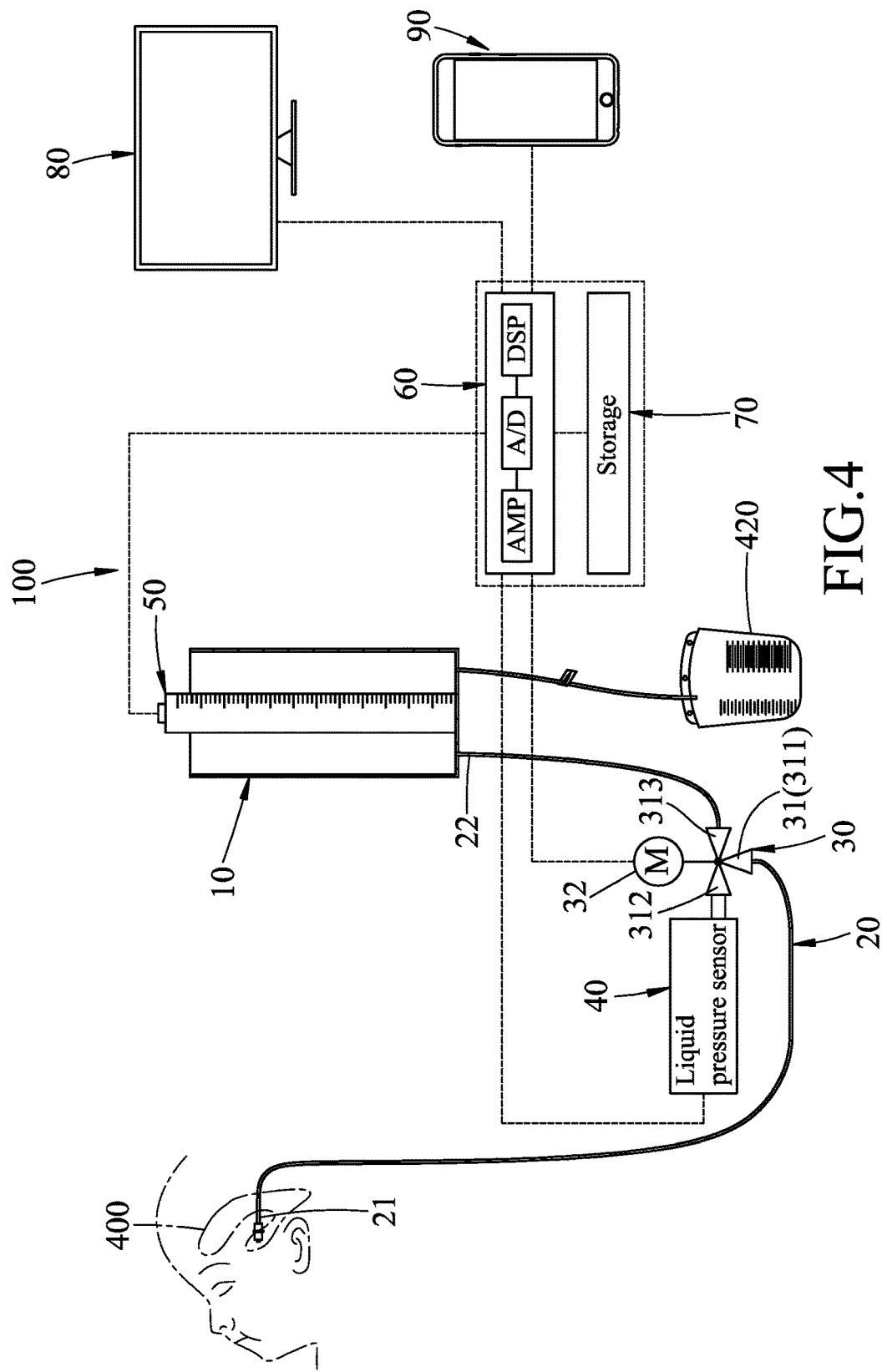
FIG. 4 is a schematic diagram illustrating a second embodiment of the automatic regulating system according to the disclosure.
Figure 5:
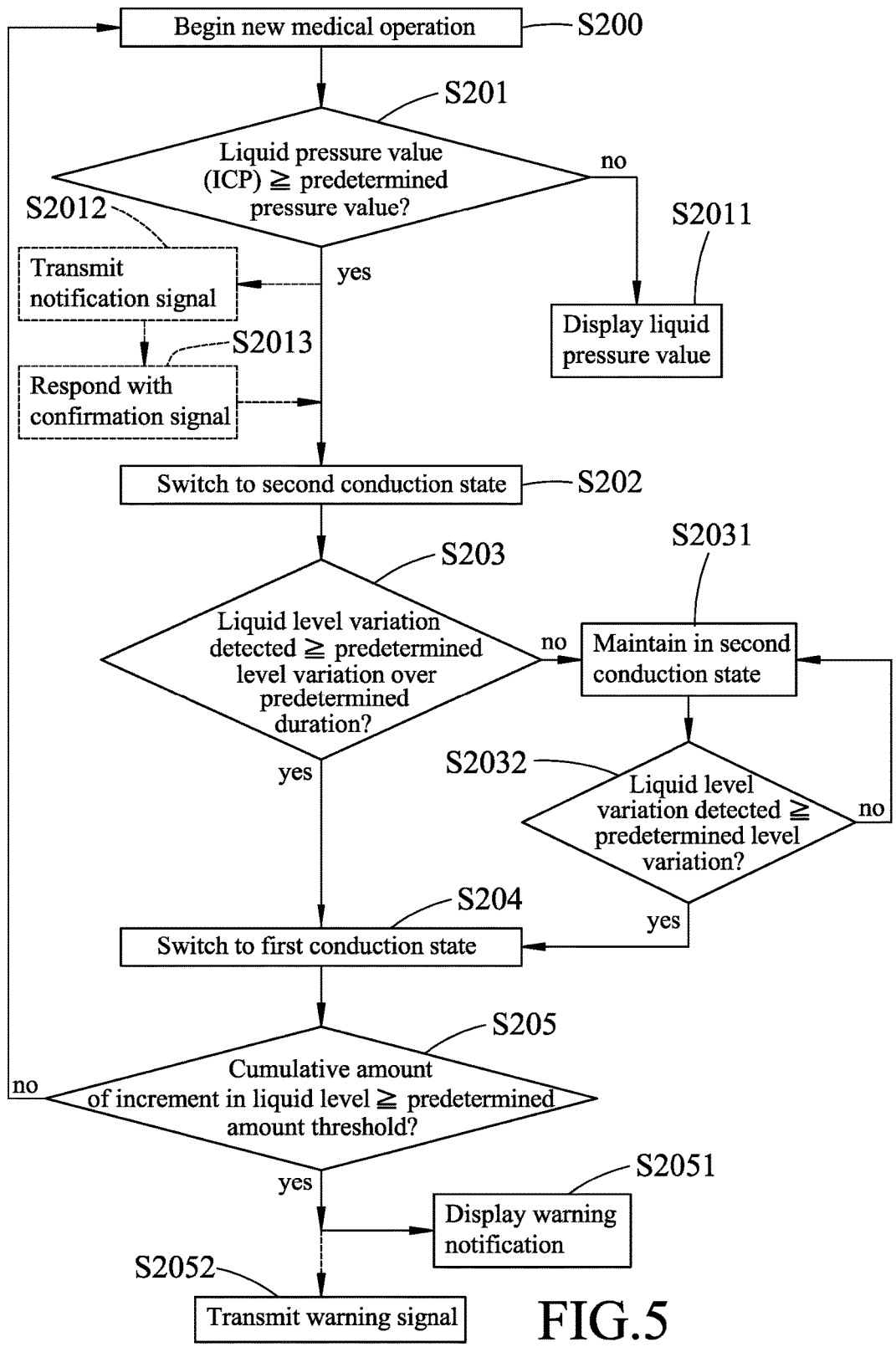
FIG. 5 is a flow chart illustrating a control flow of the second embodiment of the automatic regulating system.
Figure 6:
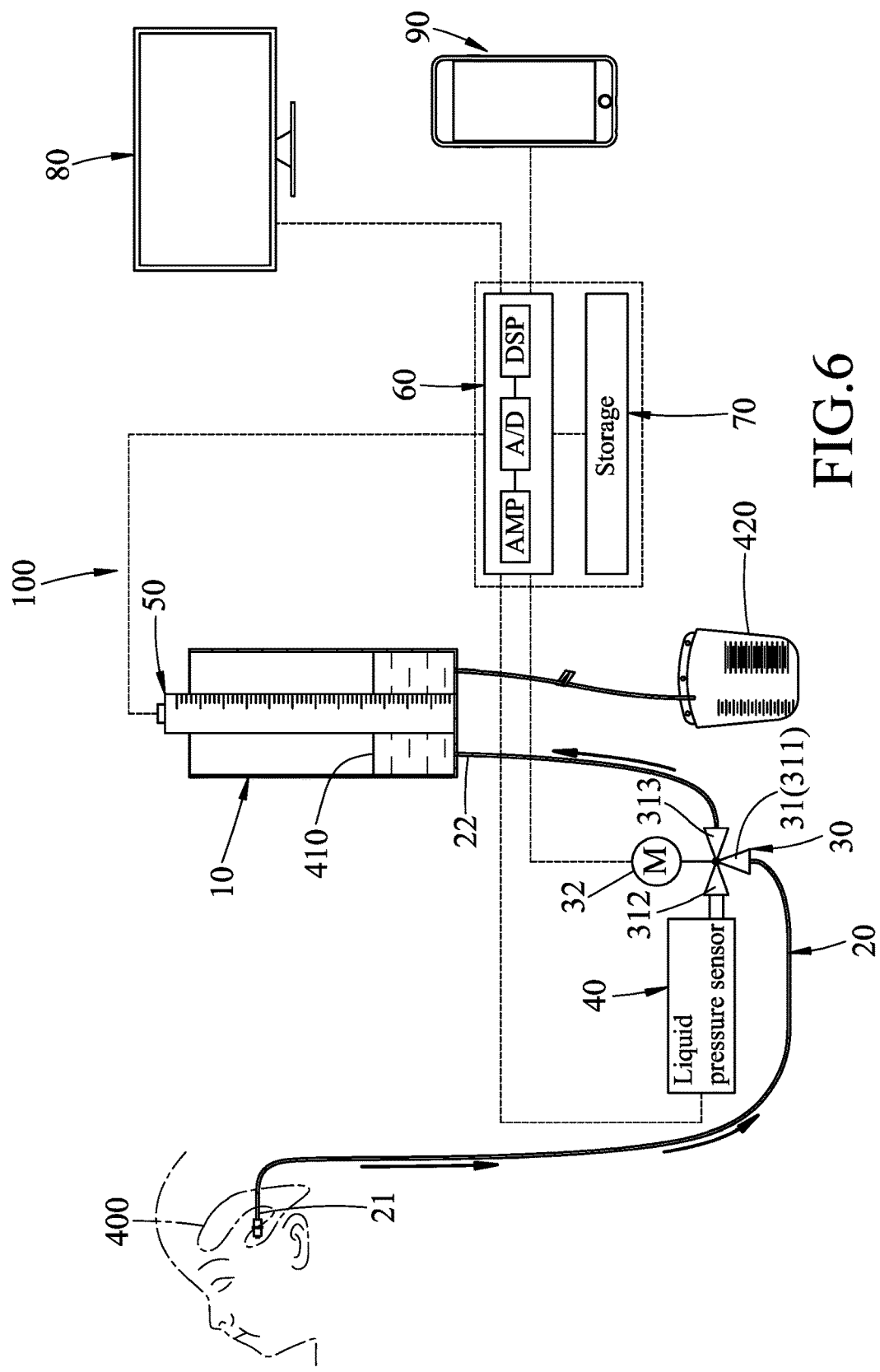
FIG. 6 is a schematic diagram illustrating drainage of liquid in human tissue into a container in the second embodiment.

Referring to FIGS. 4, 5 and 6, a second embodiment of the automatic regulating system 100 of this disclosure is illustrated. The second embodiment is similar to the first embodiment. Details of similar parts thereof are omitted herein for the sake of brevity, and parts of the second embodiment different from the first embodiment are described in the following.

In the second embodiment, the automatic regulating system 100 is configured to be connected to human tissue 400. The human tissue 400 is exemplified as a ventricle of a human brain. Liquid pressure in the ventricle is intracranial pressure (ICP) of liquid 410, i.e., cerebrospinal fluid (CSF), in the ventricle. In addition, a bottom of the container 10 has a storage bag 420 connected thereto. The storage bag 420 is capable of storing the liquid 410 collected in the container 10, but is not limited to the disclosure herein.

As illustrated by FIGS. 5 and 6, the automatic regulating system 100 is applied to maintain constant ICP of a patient, and a control flow including steps to be performed by the automatic regulating system 100 is illustrated. The first tube 21 is connected to the human tissue 400, and the three-way valve 31 is initially in the first conduction state for allowing the liquid pressure sensor 40 to measure the liquid pressure in the human tissue 400. The control flow starts from step S200, where a new medical operation begins. In step S201, the control module 60 determines whether the liquid pressure value of the liquid pressure (i.e., the ICP) in the human tissue 400 obtained by the liquid pressure sensor 40 is not smaller than the predetermined pressure value, e.g., 20 mmHg.

When it is determined by the control module 60 in step S201 that the liquid pressure value is not smaller than the predetermined pressure value, that is, the liquid pressure value of the ICP is too high, the control flow proceeds to step S202. Otherwise, when it is determined by the control module 60 in step S201 that the liquid pressure value is smaller than the predetermined pressure value, which means that the liquid pressure value of the ICP of the patient is normal, the control flow proceeds to step S2011.

In step S202, the control module 60 controls the three-way valve 31 to switch from the first conduction state to the second conduction state for allowing the liquid 410 in the human tissue 400 to flow into the container 10 by gravity. In a variation of this embodiment, a double-checking mechanism by the healthcare provider which is exemplified as steps S2012 and S2013 may be adopted for safety concerns. Prior to controlling the switch unit 30 to switch to the second conduction state, in step S2012, the control module 60 transmits a notification signal to the electronic device 90 for output of a notification by the electronic device 90 when it is determined in step S201 that the liquid pressure value obtained by the liquid pressure sensor 40 is not smaller than the predetermined pressure value. In step S2013, the healthcare provider who is notified by the notification may, depending on a condition of the patient, respond by operating the electronic device 90 to generate a confirmation signal that is to be transmitted to the control module 60. In other words, the confirmation signal is generated in response to user confirmation of the notification and of the patient's condition. Upon receiving the confirmation signal, the control module 60 performs step S202.

In step S203, the control module 60 determines whether an increment in the liquid level over a predetermined duration of drainage of the liquid 410 from the human tissue 400 is not less than the predetermined level variation. When it is determined by the control module 60 that the increment in the liquid level over the predetermined duration, e.g., 10 minutes, is less than a predetermined level variation, which means that a preset amount of the liquid 410 corresponding to the predetermined level variation, e.g., 5 mL, has not been completely drained from the human tissue 400 into the container 10 within the predetermined duration, the control flow goes to step S2013, where the control module 60 maintains the three-way valve 31 of the switch unit 30 in the second conduction state until it is determined by the control module 60 in step S2032 that the increment in the liquid level thus detected for the current medical operation is not less than the predetermined level variation. In this way, the preset amount of the liquid 410 contained in the human tissue 400 is ensured to be drained into the container 10.

When it is determined by the control module 60 in step S203 that the increment in the liquid level over the predetermined duration detected by the level sensor 50 is not less than the predetermined level variation or in step S2032 that the increment in the liquid level for the current medical operation is not less than the predetermined level variation, which means that the preset amount of the liquid 410 corresponding to the predetermined level variation has been completely drained from the human tissue 400 into the container 10, the control flow goes to step S204, where the control module 60 controls the three-way valve 31 of the switch unit 30 to switch to the first conduction state.

In step S205, after controlling the switch unit 30 to switch to the first conduction state, the control module 60 determines whether the cumulative amount of the increment in the liquid level is not smaller than a predetermined amount threshold, e.g., 15 mL. Herein, the cumulative amount of the increment is defined as the total increment amount accumulated in all medical operation (s) performed thus far on this particular patient for bringing his/her ICP back to normal.

When it is determined in step S205 that the cumulative amount of the increment in the liquid level is smaller than the predetermined amount threshold, which means that the total amount of the liquid 410 drained from the human tissue 400 into the container 10 has not exceeded a safety threshold for treatment, the control flow goes back to step S200 to begin a new medical operation.

In steps S2051 and S2052, the control module 60 controls the display 80 to display a warning notification and transmits a warning signal to the electronic device 90 for output of a warning notification accordingly by the electronic device 90 when it is determined by the control module 60 in step S205 that the cumulative amount of the increment in the liquid level is not less than the predetermined amount threshold, which means that the total amount of the liquid 410 drained from the human tissue 400 into the container 10 has reached or exceeded the safety threshold for treatment. As a result, the healthcare provider notified by the warning notification may take care of the patient in time and appropriately handle the situation.

In step S2011, the control module 60 controls the display 80 to display the liquid pressure value, so that the healthcare provider may be informed of the condition of the patient.

It should be noted that the condition of the patent, such as the liquid pressure value of the CVP and/or the ICP during the treatment may be recorded automatically by the control module 60 in the storage 70.

In brief, the control module 60 automatically controls the switching of the three-way valve 31 of the switch unit 30 between the first and second conduction states according to the liquid pressure value obtained by the liquid pressure sensor 40 and the variation in the liquid level detected by the level sensor 50, so that the preset amount of the liquid 410, e.g., the CSF, can be drained from the human tissue 400 of the patient into the container 10. As a result, the liquid pressure value of the ICP of the patient can be brought back in a normal range and maintain in the normal range. In other words, this embodiment achieves similar effect as the first embodiment.

To sum up, the automatic regulating system of this disclosure is capable of maintaining automatically and precisely constant liquid pressure in the human body and recording automatically conditions of the patient. That is to say, by the automatic regulating system of this disclosure, workload of the healthcare provider is alleviated and risk in medical treatment is mitigated. Safety of treatment is consequently enhanced.

In the description above, for the purposes of explanation, numerous specific details have been set forth in order to provide a thorough understanding of the embodiments. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. An automatic regulating system for regulation of liquid pressure in a body of a subject, the automatic regulating system configured to be connected to tissue of the subject, and comprising:
    a container configured to contain liquid;
    a tubing configured to be connected between the tissue of the subject and said container, and including a first tube which is to be in fluid communication with the tissue of the subject and a second tube which is in fluid communication with said container;
    a switch unit connected between said first tube and said second tube of said tubing;
    a liquid pressure sensor connected to said switch unit and configured to measure liquid pressure in the tissue of the subject to obtain a liquid pressure value;
    a level sensor connected to said container and configured to detect a liquid level of the liquid contained in said container; and
    a control module electrically connected to said switch unit, said liquid pressure sensor and said level sensor;
    wherein said switch unit is controllable to switch between a first conduction state, where fluid communication between said first tube and said second tube of said tubing is prevented while fluid communication between said first tube and said liquid pressure sensor is permitted for allowing said liquid pressure sensor to measure the liquid pressure in the tissue of the subject, and a second conduction state, where the fluid communication between said first tube and said liquid pressure sensor is prevented while the fluid communication between said first tube and said second tube is permitted so that the tissue of the subject is in fluid communication with said container; and
    wherein said control module is programmed to control switching of said switch unit according to the liquid pressure value obtained by said liquid pressure sensor, and a variation in the liquid level detected by said level sensor.

2. The automatic regulating system as claimed in claim 1, wherein said control module controls said switch unit to switch to the second conduction state for allowing the liquid contained in said container to flow into the tissue of the subject when it is determined by said control module that the liquid pressure value obtained by said liquid pressure sensor is not greater than a predetermined pressure value;
    said control module further controlling said switch unit to remain in the second conduction state when it is determined by said control module that a decrement in the liquid level thus detected is less than a predetermined level variation; and
    when it is determined by said control module that the decrement in the liquid level thus detected is not less than the predetermined level variation, said control module further controlling said switch unit to switch to the first conduction state and determining whether the liquid pressure value is not greater than the predetermined pressure value.

3. The automatic regulating system as claimed in claim 2, further comprising a display which is electrically connected to said control module;
    wherein said control module further controls said display to display the liquid pressure value when it is determined by said control module that the liquid pressure value is greater than the predetermined pressure value.

4. The automatic regulating system as claimed in claim 2, further comprising an electronic device which is configured to communicate with said control module;
    wherein, prior to controlling said switch unit to switch to the second conduction state, said control module transmits a notification signal to said electronic device for output of a notification by said electronic device when it is determined that the liquid pressure value obtained by said liquid pressure sensor is not greater than the predetermined pressure value; and
    wherein said control module controls said switch unit to switch to the second conduction state for allowing the liquid contained in said container to flow into the tissue of the subject when receiving from said electronic device a confirmation signal which is generated in response to user confirmation of the notification.

5. The automatic regulating system as claimed in claim 2, wherein, after determining that the decrement in the liquid level thus detected is not less than the predetermined level variation and after controlling said switch unit to switch to the first conduction state, said control module proceeds to determine whether the liquid pressure value obtained by said liquid pressure sensor is not greater than the predetermined pressure value when it is determined that a cumulative amount of the decrement in the liquid level is smaller than a predetermined amount threshold.

6. The automatic regulating system as claimed in claim 5, further comprising a display which is electrically connected to said control module;
wherein said control module further controls said display to display a warning notification when it is determined by said control module that the cumulative amount of the decrement in the liquid level is not less than the predetermined amount threshold.

7. The automatic regulating system as claimed in claim 5, further comprising an electronic device which is configured to communicate with said control module;
wherein said control module transmits a warning signal to said electronic device for output of a warning notification by said electronic device when it is determined by said control module that the cumulative amount of the decrement in the liquid level is not less than the predetermined amount threshold.

8. The automatic regulating system as claimed in claim 5, further comprising a storage which is electrically connected to said control module, and is configured to store the predetermined pressure value, the predetermined level variation, and the predetermined amount threshold.

9. The automatic regulating system as claimed in claim 2, wherein said switch unit includes a three-way valve connected to said liquid pressure sensor and said first tube and said second tube of said tubing, and a step motor electrically connected to said control module and configured to drive said three-way valve to switch between the first conduction state and the second conduction state.

10. The automatic regulating system as claimed in claim 2, wherein the decrement in the liquid level detected by said level sensor is defined as a decrement in the liquid level over a predetermined duration of administration of the liquid to the tissue of the subject.

11. The automatic regulating system as claimed in claim 1, wherein said control module controls said switch unit to switch to the second conduction state for allowing liquid in the tissue of the subject to flow into said container when it is determined by said control module that the liquid pressure value obtained by said liquid pressure sensor is not smaller than a predetermined pressure value;
said control module further controlling said switch unit to remain in the second conduction state when it is determined by said control module that an increment in the liquid level thus detected is less than a predetermined level variation; and
when it is determined by said control module that the increment in the liquid level thus detected is not less than the predetermined level variation, said control module further controlling said switch unit to switch to the first conduction state and determining whether the liquid pressure value is not smaller than the predetermined pressure value.

12. The automatic regulating system as claimed in claim 11, further comprising a display which is electrically connected to said control module;
wherein said control module further controls said display to display the liquid pressure value when it is determined by said control module that the liquid pressure value is smaller than the predetermined pressure value.

13. The automatic regulating system as claimed in claim 11, further comprising an electronic device which is configured to communicate with said control module;
wherein, prior to controlling said switch unit to switch to the second conduction state, said control module transmits a notification signal to said electronic device for output of a notification by said electronic device when it is determined that the liquid pressure value obtained by said liquid pressure sensor is not smaller than the predetermined pressure value; and
wherein said control module controls said switch unit to switch to the second conduction state for allowing the liquid contained in the tissue of the subject to flow into said container when receiving from said electronic device a confirmation signal which is generated in response to user confirmation of the notification.

14. The automatic regulating system as claimed in claim 11, wherein, after determining that the increment in the liquid level thus detected is not less than the predetermined level variation and after controlling said switch unit to switch to the first conduction state, said control module proceeds to determine whether the liquid pressure value obtained by said liquid pressure sensor is not smaller than the predetermined pressure value when it is determined that a cumulative amount of the increment in the liquid level is less than a predetermined amount threshold.

15. The automatic regulating system as claimed in claim 14, further comprising a display which is electrically connected to said control module;
wherein said control module further controls said display to display a warning notification when it is determined by said control module that the cumulative amount of the increment in the liquid level is not less than the predetermined amount threshold.

16. The automatic regulating system as claimed in claim 14, further comprising an electronic device which is configured to communicate with said control module;
wherein said control module transmits a warning signal to said electronic device for output of a warning notification by said electronic device when it is determined by said control module that the cumulative amount of the increment in the liquid level is not less than the predetermined amount threshold.

17. The automatic regulating system as claimed in claim 14, further comprising a storage which is electrically connected to said control module, and to store the predetermined pressure value, the predetermined level variation, and the predetermined amount threshold.

18. The automatic regulating system as claimed in claim 11, wherein said switch unit includes a three-way valve connected to said liquid pressure sensor and said first tube and said second tube of said tubing, and a step motor electrically connected to said control module and configured to drive said three-way valve to switch between the first conduction state and the second conduction state.

19. The automatic regulating system as claimed in claim 11, wherein the increment in the liquid level detected by said level sensor is defined as an increment in the liquid level over a predetermined duration of drainage of the liquid from the tissue of the subject.

20. The automatic regulating system as claimed in claim 1, wherein said level sensor is a resistive liquid level sensor.

* * * * *